United States Patent
Sun et al.

(10) Patent No.: US 7,368,458 B2
(45) Date of Patent: *May 6, 2008

(54) BICYCLIC HETEROCYCLES AS CANNABINOID RECEPTOR MODULATORS

(75) Inventors: Chongqing Sun, East Windsor, NJ (US); William R. Ewing, Yardley, PA (US); Yanting Huang, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 9 days.

This patent is subject to a terminal disclaimer.

(21) Appl. No.: 11/330,541

(22) Filed: Jan. 12, 2006

(65) Prior Publication Data

US 2006/0155126 A1 Jul. 13, 2006

Related U.S. Application Data

(60) Provisional application No. 60/643,363, filed on Jan. 12, 2005.

(51) Int. Cl.
  C07D 471/02 (2006.01)
  C07D 487/02 (2006.01)
  A61K 31/4375 (2006.01)
(52) U.S. Cl. .................................. 514/300; 546/122
(58) Field of Classification Search ................ 546/122; 514/300
  See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,379,785 A | 4/1983 | Weyer et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,639,436 A | 1/1987 | Junge et al. | |
| 4,647,576 A | 3/1987 | Hoefle et al. | |
| 4,681,893 A | 7/1987 | Roth | |
| 4,686,237 A | 8/1987 | Anderson | |
| 4,759,923 A | 7/1988 | Buntin et al. | |
| 4,871,721 A | 10/1989 | Biller | |
| 4,904,769 A | 2/1990 | Rauenbusch | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,354,772 A | 10/1994 | Kathawala | |
| 5,385,929 A | 1/1995 | Bjorge et al. | |
| 5,447,954 A | 9/1995 | Gribble et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |
| 5,594,016 A | 1/1997 | Ueno et al. | |
| 5,612,359 A | 3/1997 | Murugesan | |
| 5,686,104 A | 11/1997 | Mills et al. | |
| 5,691,322 A | 11/1997 | Robl | |
| 5,698,527 A | 12/1997 | Kim | |
| 5,712,396 A | 1/1998 | Magnin et al. | |
| 5,753,675 A | 5/1998 | Wattanasin | |
| 5,770,615 A | 6/1998 | Cheng et al. | |
| 5,776,983 A | 7/1998 | Washburn et al. | |
| 5,990,109 A | 11/1999 | Chen et al. | |
| 6,043,265 A | 3/2000 | Murugesan et al. | |
| 6,184,231 B1 | 2/2001 | Hewawasam et al. | |
| 6,414,002 B1 | 7/2002 | Cheng et al. | |
| 6,635,626 B1 | 10/2003 | Barrish et al. | |

FOREIGN PATENT DOCUMENTS

| | | |
|---|---|---|
| EP | 0 142 146 | 8/1988 |
| EP | 0 221 025 | 5/1997 |
| EP | 0 818 448 B1 | 1/1998 |
| EP | 0 675 714 B1 | 1/1999 |
| EP | 1 142 877 | 10/2001 |

(Continued)

OTHER PUBLICATIONS

Biiller, S. et al., "Squalene Synthase Inhibitors", Current Pharmaceutical Design, vol. 2, pp. 1-40 (1996).

(Continued)

*Primary Examiner*—Kahsay T Habte
(74) *Attorney, Agent, or Firm*—Rosemary M. Miano; Maureen G. Gibbons

(57) ABSTRACT

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I:

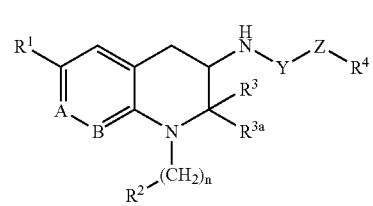

including all prodrugs, pharmaceutically acceptable salts and stereoisomers, $R^1$, $R^2$, $R^3$, $R^{3a}$, $R^4$, A, B, n, Y and Z are described herein.

18 Claims, No Drawings

FOREIGN PATENT DOCUMENTS

| | | |
|---|---|---|
| EP | 1 022 272 B1 | 6/2004 |
| EP | 0 992 496 | 8/2005 |
| FR | 2 596 393 | 5/1986 |
| GB | 2 205 837 | 12/1988 |
| GB | 2 304 106 | 3/1997 |
| WO | WO 86/03488 | 6/1986 |
| WO | WO 86/07054 | 12/1986 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |
| WO | WO 2005/020987 | 3/2005 |
| WO | WO 2005020987 A1 * | 3/2005 |
| WO | WO 2005/123685 | 12/2005 |

OTHER PUBLICATIONS

Biller, S. et al., "Isoprenoid (Phosphinylmethyl) phoshonates as Inhibitors of Squalene Synthetase", J. of Medicinal Chemistry, vol. 31(10), pp. 1869-1871 (1988).

Colombo, G. et al., "Appetite Suppression and Weight Loss after the Cannabinoid Antagonist SR 141716 ", vol. 63, 8, pp. 113-117, (1998).

Corey, E. et al., "Application of Unreactive Analogs of Terpenoid Pyrophosphates to Studies of Multistep Biosynthesis. Demonstration that "Prequalene Pyrophosphate" is an Essential Intermediate on the Path to Squalene", J of the Amer. Chemical Society, vol. 98(5), pp. 1291-1293 (1976).

Davidsen, S. et al., "$N$-(Acyloxyalkyl) pyridinium Salts as Soluble Prodrugs of a Potent Platelet Activating Factor Antagonist", J. of Medicinal Chemistry, vol. 37(26), pp. 4423-4429 (1994).

DiMarzo, V. et al., "Leptin-regulated endocannabinoids are involved in maintaining food intake", Nature, vol. 410, pp. 822-825 (2001).

Ettmayer, P. et al., "Lessons Learned from Marketed and Investigational Prodrugs", J. of Medicinal Chemisry, vol. 47(10), pp. 2393-2404 (2004).

Galiegue, S. et al., "Expression of central and peripheral cannabinoid receptors in human immune tissues and leukocyte subpopulations", Eur. J. Biochem., vol. 232, pp. 54-61 (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Glass, M. et al., "Cannabinoid receptors in the Human Brain: A detailed anatomical and quantitative Autoradiographic Study in the Fetal Neonatal and Adult Human Brain", Neuroscience, vol. 77(2), pp. 299-318 1997.

Hara, S., "Ileal Na$^+$/bile acid cotransporter inhibitors", Drugs of the Future, vol. 24(4), pp. 425-430 (1999).

Hildebrandt, A. et al., "Antiobesity effects of chronic cannabinoid $CB_1$ receptor antagonist treatment in diet-induced obese mice", Eur. J. of Pharmacology, vol. 462, pp. 125-132 (2003).

Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12), pp. 4313-4321 (1992).

Hollenbaugh, D. et al., "Cleavable CD40lg fusion proteins and the binding to sgp39", J. of Immunological Methods, vol. 188, pp. 1-7 (1995).

Krause, B. et al. "ACAT Inhibitors: Physiologic Mechanisms for Hypolipidemic and Anti-Atherosclerotic Activities in Experimental Animals", Inflammation Mediators and Pathways, pp. 173-198 (1995).

Ljung, B. et al., "AZ 242, a novel PPARα/γ agonist with beneficial effects on insulin resistance and carbohydrate and lipid metabolism in ob/ob mice and obese Zucker rats". J. of Lipid Research, vol. 43, pp. 1855-1863 (2002).

Matsuda, L. et al., "Structure of a cannabinoid receptor and functional expression of the cloned cDNA", Nature, vol. 346, pp. 561-563 (1990).

McClard, R. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Moreland, L. et al., "Treatment of Rheumatoid Arthritis with a recombinant Human Tumor Necrosis Factor Receptor (p75)-Fc Fusion Protein", The New England J. of Medicine, vol. 337(3), pp. 141-147 (1997).

Munro, S. et al., "Molecular characterization of a peripheral receptor for cannabinoids", Nature, vol. 365, pp. 61-65 (1993).

Nicolosi, R. et al., "ACAT Inhibitor, CI-1011 is effective in the prevention and regression of aortic fatty streak area in hamsters", Atherosclerosis, vol. 137, pp. 77-85 (1998).

Ortiz de Montellano, et al., "Inhibition of Squalene Synthetase by Farnesyl Pyrophosphate Analogues", J. of Medicinal Chemistry, vol. 20(2), pp. 243-249 (1977).

Rosenblum, S. et al., "Discovery of 1-(4-Fluorophenyl)-($3R$)-[3-(4-fluorophenyl)-(3$S$)-hydroxypropyl]-(4$S$)-(4-hydroxyphenyl)-2-azetidinone (SCH 58235)" A Designed, Potent, Orally Active Inhibitor of Cholesterol Absorption, J. Med. Chem., vol. 41, pp. 973-980 (1998).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Salisbury, B. et al., "Hypocholesterolemic activity of a novel inhibitor of cholesterol absorption. SCH 48461", Atherosclerosis, vol. 115, pp. 45-63 (1995).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6(1), pp. 47-50 (1996).

Sorbera, L. et al., "Avasimibe. Treatment of Lipoprotein Disorders ACAT Inhibitor", Drugs of the Future, vol. 24(1), pp. 9-15 (1999).

Stout, D., "Inhibitors of Acyl-CoA: Cholesterol $O$-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT). 7 Development of a Series of Substituted $N$-Phenyl-$N$-[(1-phenylcyclopentyl)-methyl]ureas with Enhanced Hypocholestrolemic Activity".

Trillou, C.R. et al., "Anti-obesity effect of SR141716, a CB1 receptor antagonist, in diet-induced obese mice", Am. J. Physiol Regul Integr Comp Physiol, vol. 284, pp. R345-R353 (2003).

Williams, C. et al., "Anandamide induces overeating: mediation by central cannabinoid (CB1) receptors", Psychopharmacology, vol. 143, pp. 315-317 (1999).

Yajima, K. et al., "Combination therapy with PPARγ and PPARα agonists increases glucose-stimulated insulin secretion in db/db/ mice", Am J Physiol Endocrinol Metab, vol. 284, pp. E966-E971 (2003).

* cited by examiner

BICYCLIC HETEROCYCLES AS CANNABINOID RECEPTOR MODULATORS

RELATED APPLICATION

This application claims priority benefit under Title 35 § 119(e) of U.S. Provisional Application No. 60/643,363, filed Jan. 12, 2005, the contents of which are herein incorporated by reference.

BACKGROUND

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I

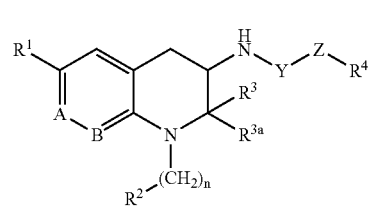

including all prodrugs, pharmaceutically acceptable salts and stereoisomers, $R^1$, $R^2$, $R^3$, $R^{3a}$, $R^4$, A, B, n, Y and Z are described herein:

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carboxamido, carbonyl, alkenyl, alkynyl, nitro, amino, alkoxy, aryloxy, arylalkyloxy, heteroaryloxy, amido, —OPO₃H, —OSO₃H, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chains of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chains of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

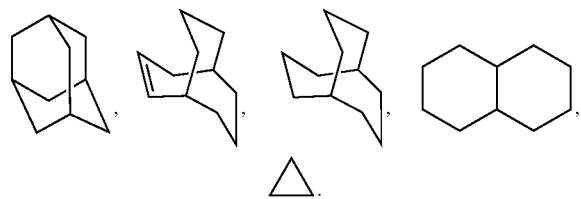

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

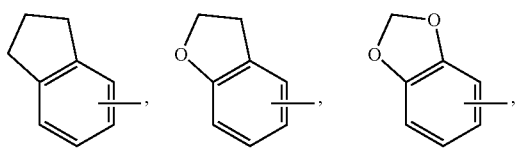

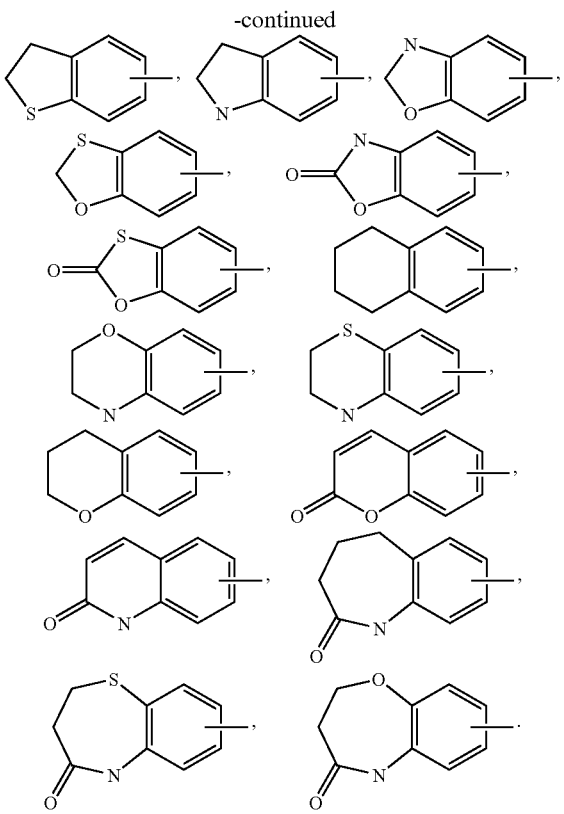

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

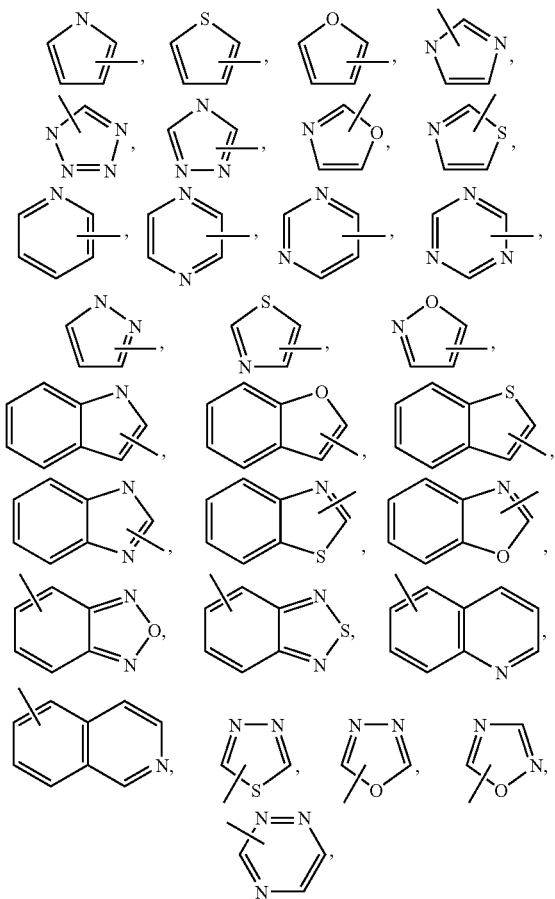

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a —CH$_2$—group.

The term "nitro," as used herein, refers to a —NO$_2$ group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$-C$_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of formula I with an open valence for further substitution wherein such substitution can, upon biotransformation, generate a compound of formula I. Examples of such functional groups of bioactive metabolites include, but are not limited to, —OH, —NH or functional groups wherein the hydrogen can be replaced with a functional group such as —PO$_3$H$_2$ for example, which, upon biotransformation generates an —OH or —NH functional group of a compound of formula I.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. Prodrug esters may also include—but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as—but not limited to—favorable aqueous solubility or in vivo exposure to the bioactive component formula I.

The term "prodrug" as employed herein includes functionalization of bioactive amine- or hydroxyl-containing compounds of formula I to form alkyl-, acyl-, sulfonyl-, phosphoryl-, or carbohydrate-substituted derivatives. Such derivatives are formed by reacting compounds of formula I with alkylating-, acylating-, sulfonylating-, or phosphorylating reagents employing procedures known to those skilled in the art. Alkylation of amines of formula I may result in—but are not limited to—derivatives that include spacer units to other prodrug moieties such as substituted alkyoxymethyl-, acyloxymethyl-, phosphoryloxymethyl-, or sulfonyloxymethyl-groups. Alkylation of amines of formula I may result in the generation of quarternary amine salts that act in vivo to provide the bioactive agent (i.e., the compound of formula I).

Preferred prodrugs consist of a compound of formula I where a pendant hydroxyl is phosphorylated to generate a phosphate derivative. Such a prodrug may also include a spacer group between the compound of formula I and the phosphate group, such as a methyleneoxy-group. Methods to generate such a prodrug from a compound of formula I are known to those skilled in the art, and are listed in the references below.

Preferred prodrugs also consist of a compound of formula I where a pendant amine, such as a pyridine group, is alkylated with a group, such as methyl, to form a quarternary ammonium ion salt. Methods to generate such a prodrug from a compound of formula I are known to those skilled in the art, and are listed in the references below.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch. 5, pgs 113-191 (Harwood Academic Publishers, 1991);

d) *Hydrolysis in Drug and Prodrug Metabolism*, B. Testa and J. M. Mayer, (Verlag Helvetica Chimica Acta AG, Zurich, Switzerland; Wiley-VCH, Weinheim, Federal Republic of Germany, 2003);

e) Ettmayer, P.; Amidon, G. L.; Clement, B.; Testa, B. "Lessons Learned from Marketed and Investigational Prodrugs" *J. Med. Chem.* 2004, 47 (10), 2393-2404; and f) Davidsen, S. K. et al. "N-(Acyloxyalkyl)pyridinium Salts as Soluble Prodrugs of a Potent Platelet Activating Factor Antagonist" *J. Med. Chem.* 1994, 37 (26), 4423-4429.

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed in the Schemes, Examples and elsewhere herein:

AcOH=acetic acid
Boc=tert-butoxycarbonyl
Cbz=benzyloxycarbonyl
DIPEA=N,N-diisopropylehtylamine
DMF=N,N-dimethylformamide
EtOAc=ethyl acetate DPPA=diphenylphosphoryl azide
Et₃N=triethylamine
Et₂O=diethyl ether
HPLC or LC=high performance liquid chromatography
MeOH=methanol
MS or Mass Spec=mass spectrometry
NaCl=sodium chloride
NaHCO₃=sodium bicarbonate
Na₂SO₄=sodium sulfate
NaOH=sodium hydroxide
PG=protecting group
PXPd=dichloro-bis(chloro-di-tert-butylphosphine)palladium
RT=room temperature
TMEDA=N,N,N',N'-tetramethylethylenediamine
TFA=trifluoroacetic acid
THF=tetrahydrofuran
min=minute(s)
h=hour(s)
L=liter
mL=milliliter
μL=microliter
g=gram(s)
mg=milligram(s)
mol=moles
mmol=millimole(s)
nM=nanomolar Compounds of the present invention may be prepared by procedures illustrated in the accompanying schemes.

METHODS OF PREPARATION

The compounds of the present invention may be prepared by methods such as those illustrated in the following Scheme 1 to 2. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, $R^1$, $R^2$, $R^3$, $R^{3a}$, $R^4$, A, B, n, Y and Z are as described for a compound of formula I.

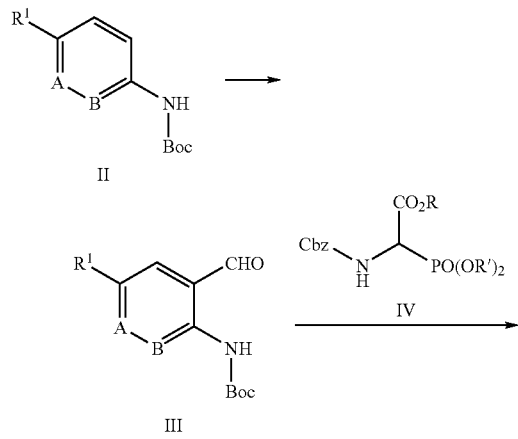

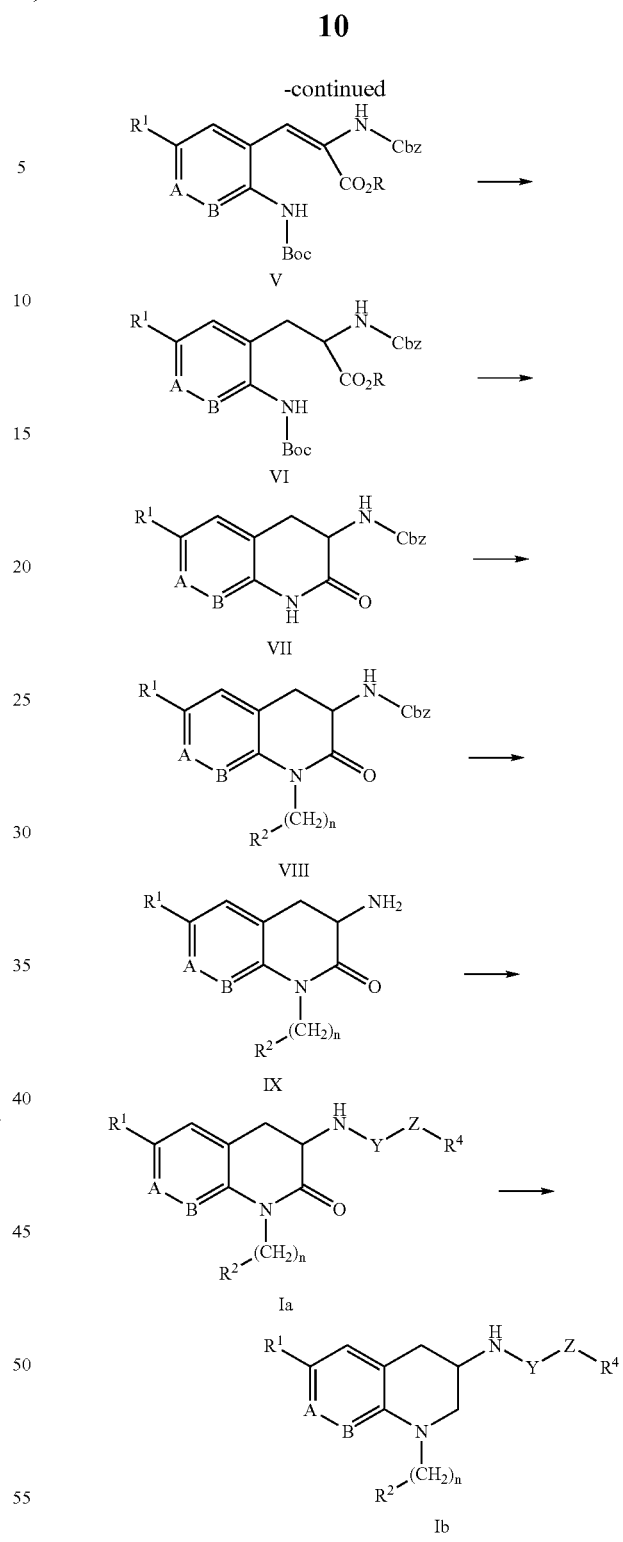

Compounds of formula II are either commercially available or can be readily prepared by one skilled in the art. Compounds of formula III can be prepared by treating intermediate II with an organolithium reagent, such as n-butyllithium in the presence of a diamine (e.g., N,N,N', N'-tetramethylethylenediamine) at low temperature, preferably below 70° C. in an aprotic polar solvent (e.g., THF), followed by addition of a formylating reagent, such as DMF or N-formyl piperidine. Compounds of formula V can be prepared by reacting of intermediate III with a functionalized phosphonate ester IV in the presence of a strong base (e.g., sodium hydride) in an aprotic polar solvent (e.g., THF). Intermediate IV can be readily prepared by one skilled in the art. Compounds of formula VI can be prepared via catalytic hydrogenation under medium hydrogen pressure (e.g., 80 psi) in the presence of a platinum catalyst. Compounds of formula VII can be prepared by removing the Boc group in intermediate VI with a strong acid (e.g., trifluoroacetic acid in dichloromethane), followed by refluxing in the presence of catalytic amount of an acid, such as p-toluenesulfonic acid. Compounds of formula VIII can be prepared by reacting intermediate VII with an alkylhalide in the presence of a base (e.g., cesium carbonate) or with an arylhalide via a transition metal (e.g., palladium or copper) mediated reaction. Compounds of formula IX can be prepared by removing the Cbz group in intermediate VIII by catalytic hydrogenolysis or a Lewis acid (e.g., iodotrimethylsilane). Compounds of formula Ia can be prepared by reacting intermediate IX with an acyl chloride or a carboxylic acid (for formation of an amide), or a chloroformate (for formation of a carbamate), or an isocyanate (for formation of a urea), or a sulfonyl chloride (for formation of a sulfonamide), or a sulfamoyl chloride (for formation of a sulfamide). Compounds of formula Ib can be prepared from compound Ia in the presence of a reducing reagent (e.g., borane-THF complex or lithium aluminum hydride/THF).

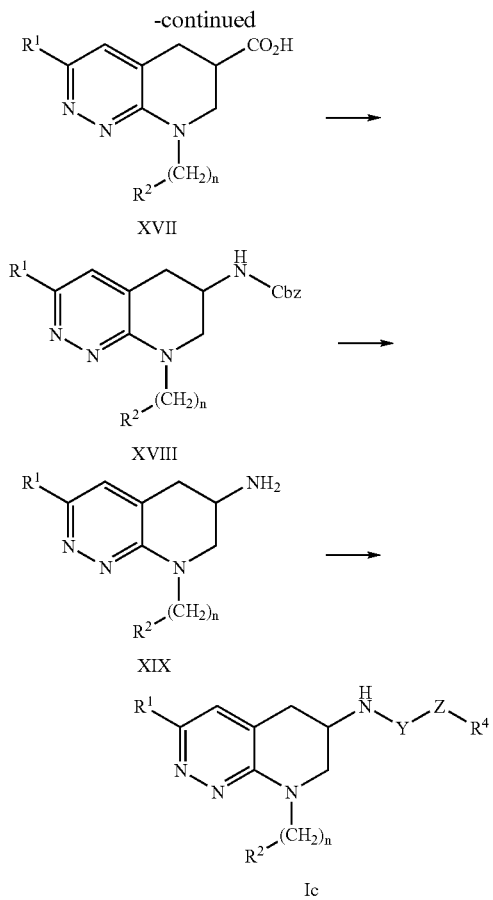

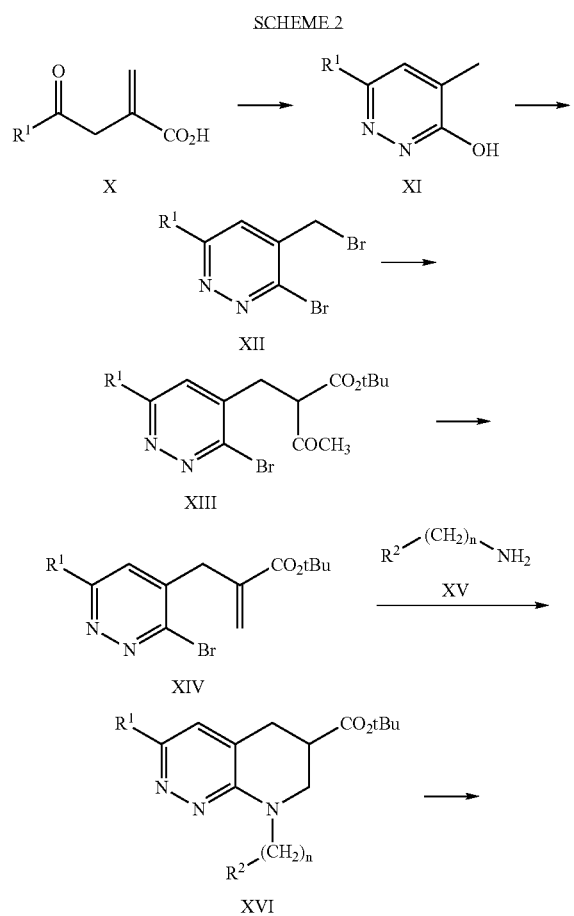

SCHEME 2

Compounds of formula X can be prepared by methods known in the literature or by one skilled in the art. Treatment of X with hydrazine in refluxing methanol provides pyridazinone XI. Reaction with excess $POBr_3$ at 120° C. leads to dibromide XII. Alkylation of tert-butyl acetoacetate with dibromide XII in the presence of a base, such as potassium carbonate or 2-tert-butylimino-2-diethylamino-1,3-dimethylperhydro-1,3,2-diazaphosphorine provides ketoester XIII. Reaction of the anion of XIII (formed with lithium bis (trimethylsilyl)-acetamide) and formaldehyde provides α,β-unsaturated ester XIV. Cyclization of XIV with amine XV in refluxing isopropanol leads to pyrido[2,3-c]pyridazine XVI. Amine XV is either commercially available or can be prepared by one skilled in the art. Removal of the tert-butyl ester in intermediate XVI with a strong acid, such as TFA provides acid intermediate XVII. Treatment of XVII under Curtius reaction conditions, such as diphenylphosphoryl azide and benzyl alcohol provides XVIII. Removal of the Cbz group in intermediate XVIII by catalytic hydrogenolysis or a Lewis acid (e.g., iodotrimethylsilane) provides amine XIX. Compounds of formula Ic can be prepared by reacting amine XIX with an acyl chloride or a carboxylic acid (for formation of an amide), or a chloroformate (for formation of a carbamate), or an isocyanate (for formation of a urea), or a sulfonyl chloride (for formation of a sulfonamide), or a sulfamoyl chloride (for formation of a sulfamide).

EXAMPLES

The following Examples serve to better illustrate, but not limit, some of the preferred embodiments of the invention.

Analytical HPLC and HPLC/MS Methods Employed in Characterization of Examples.

Analytical HPLC was performed on Shimadzu LC10AS liquid chromatographs.

Analytical HPLC/MS was performed on Shimadzu LC10AS liquid chromatographs and Waters ZMD Mass Spectrometers using the following methods:

Method A. Linear Gradient of 0 to 100% Solvent B Over 4 min, with 1 min Hold at 100% B
  UV visualization at 220 nm
  Column: Phenomenex Luna C18 4.6×50 mm
  Flow rate: 4 ml/min
Solvent A: 0.1% trifluoroacetic acid, 90% water, 10% methanol
Solvent B: 0.1% trifluoroacetic acid, 90% methanol, 10% water Method B. Linear Gradient of 0 to 100% Solvent B Over 8 min, with 3 min Hold at 100% B
  UV visualization at 220 nm
  Column: Phenomenex Luna C18 4.6×75 mm or Zorbax SB C18 4.6×75 mm
  Flow rate: 2.5 ml/min
Solvent A: 0.2% phosphoric acid, 90% water, 10% methanol
Solvent B: 0.2% phosphoric acid, 90% methanol, 10% water Method C. Linear Gradient of 0 to 100% Solvent B Over 8 min, with 3 min Hold at 100% B
  UV visualization at 220 nm
  Column: Phenomenex Luna C18 4.6×75 mm or Zorbax SB C18 4.6×75 mm
  Flow rate: 2.5 mil/min
Solvent A: 0.1% trifluoroacetic acid, 90% water, 10% acetonitrile
Solvent B: 0.2% trifluoroacetic acid, 90% acetonitrile, 10% water NMR Employed in Characterization of Examples.

$^1$H NMR spectra were obtained with Bruker or JOEL fourier transform spectrometers operating at the following frequencies: $^1$H NMR: 400 MHz (Bruker), or 400 MHz (JOEL); $^{13}$C NMR: 100 MHz (Bruker), or 100 MHz (JOEL). Spectra data are reported as Chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for $CD_2HSOCD_3$, 3.30 ppm for $CD_2HOD$, 7.24 ppm for $CHCl_3$, 39.7 ppm for $CD_3SOCD_3$, 49.0 ppm for $CD_3OD$, 77.0 ppm for $CDCl_3$). All $^{13}$C NMR spectra were proton decoupled.

Example 1

Preparation of N-(1-Benzyl-2-oxo-6-phenyl-1,2,3,4-tetrahydro-1,8-naphthyridin-3-yl)benzenesulfonamide

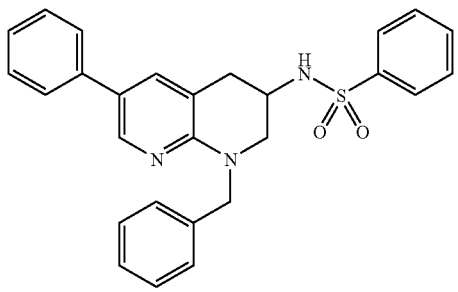

1A. Preparation of Methyl 2-(benzyloxycarbonylamino)-2-(diethoxyphosphoryl)acetate

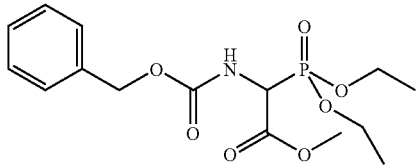

The title compound was prepared from benzyl carbamate and 2-oxoacetic acid monohydrate following literature procedures.

1B. Preparation of tert-Butyl 5-bromopyridin-2-ylcarbamate

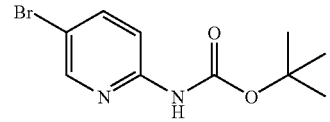

To a solution of 2-amino-5-bromopyridine (8.65 g, 50 mmol) in THF (100 mL) at 0° C. was added sodium bis(trimethylsilyl)amide (1 M solution in THF, 105 mL, 105 mmol). After addition, the reaction was stirred at 0° C. for 5 min, and then di-tert-butyl dicarbonate (12 g, 55 mmol) was added in several portions. After addition, the reaction was stirred at RT for 30 min, and then diluted with water (60 mL) and neutralized by adding ice-cold 1N HCl (about 90 mL) to pH=7~8. The resultant mixture was extracted with EtOAc (3×100 mL). The combined organic layers were washed with saturated NaCl. The organic layer was dried ($Na_2SO_4$), filtered and concentrated. The resulting residue was purified by silica gel (330 g) column chromatography eluting with a gradient of EtOAc (0-50%) in hexane to give the title compound as an off-white solid (11.6 g, 85%). LC/MS (method A): retention time=3.47 min, (M+H-tBu))$^+$=217.

1C. Preparation of tert-Butyl 5-phenylpyridin-2-ylcarbamate

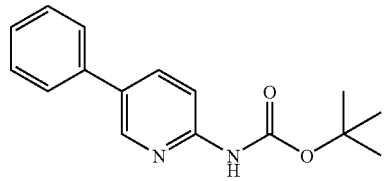

To a solution of 1B (7.65 g, 28 mmol) in THF (50 mL)-MeOH (50 mL) at RT was added phenylboronic acid (6.83 g, 56 mmol), PXPd (500 mg, 0.93 mmol), followed by $K_2CO_3$ (15.5 g, 112 mmol). The reaction mixture was stirred at 70° C. in a preheated oil bath for 1 h. After this time, the reaction mixture was cooled to RT. The reaction mixture was poured into water (100 mL), and the resultant mixture was extracted with EtOAc (3×100 mL). The combined organic layers were washed with saturated NaCl. The organic layer was dried ($Na_2SO_4$), filtered and concentrated. The resulting residue was purified by silica gel (120 g) column chromatography eluting with a gradient of EtOAc (0-60%) in hexane to give the title compound as an off-white solid (5.4 g, 72%). LC/MS (method A): retention time=3.07 min, (M+H)$^+$=271.

1D. Preparation of tert-Butyl 3-formyl-5-phenylpyridin-2-ylcarbamate

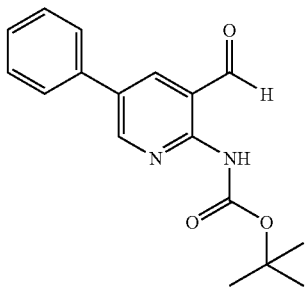

A solution of 1C (2.40 g, 8.88 mmol) in dry THF (35 mL) and TMEDA (3.35 mL, 22.2 mmol) under argon was cooled to −72° C. and treated dropwise with n-butyllithium (2.5 M in hexanes, 8.9 mL, 22.2 mmol) at such a rate so that the temperature did not exceed −65° C. Upon completion of the addition, the reaction was stirred at −72° C. for an additional 15 min and then at −20° C. for 1.5 h. The reaction was cooled again to −72° C., and dry DMF (1.4 mL, 17.8 mmol) was added while the temperature was maintained below −65° C. The mixture was allowed to stir at RT for 30 min. After this time, no starting material was detected by LC-MS. The solution was cooled to 0° C. and quenched by the addition of 1 M aqueous HCl to bring the pH to 6-8. The reaction was stirred at RT for 15 min, extracted with EtOAc (3×100 mL). The combined organic layers were washed with saturated NaCl, dried over $Na_2SO_4$, filtered, and evaporated under reduced pressure. The residue was purified by silica gel (110 g) column chromatography, eluting with a gradient of EtOAc (0-100%) in hexane to give the title compound as a yellow solid (1.1 g, 42%). LC/MS (method A): retention time=3.43 min, $(M+H-tBu)^+=243$.

1E. Preparation of (Z)-Methyl 2-(benzyloxycarbonylamino)-3-(2-(tert-butoxycarbonyl amino)-5-phenylpyridin-3-yl)acrylate

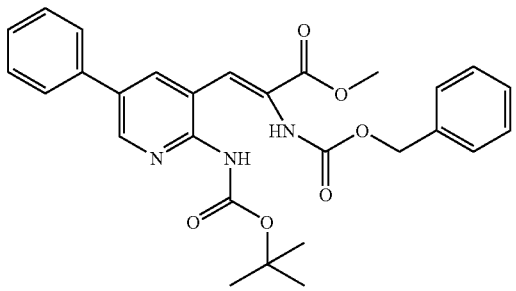

To a slurry of 60% of sodium hydride (156 mg, 3.90 mmol) in THF (8 nL) at 0° C. was added 1A (1.2 g, 3.34 mmol) in several portions over 10 min. The reaction mixture was then brought to RT for 20 min, then cooled again at 0° C. A suspension of 1D (830 mg, 2.78 mmol) in THF (10 mL) was added over 10 min at 0° C., then the reaction was warmed up to RT. After stirring for 20 min, the reaction was quenched with water (30 mL). The aqueous layer was extracted with EtOAc (50 mL×2). The combined organics were dried ($Na_2SO_4$), filtered and concentrated. The resulting residue was triturated with $CH_2Cl_2$-hexanes to give the title compound (620 mg). The mother liquid was concentrated and the resulting residue was purified by silica gel (110 g) column chromatography eluting with a gradient of EtOAc (0-60%) in hexane to give additional 130 mg of the title compound (total 750 mg, 54%) as an off-white solid. LC/MS (method A): retention time=3.40 min, $(M+H)^+=504$.

1F. Preparation of Methyl 2-(benzyloxycarbonylamino)-3-(2-(tert-butoxycarbonyl amino)-5-phenylpyridin-3-yl)propanoate

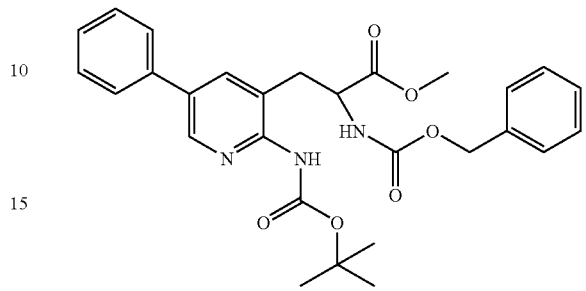

A suspension of 1E (560 mg, 1.11 mmol) and 5% wt. platinium on activated carbon (500 mg) in THF (90 mL) and MeOH (90 mL) was stirred at RT under $H_2$ at 80 psi for 2 days. After this time, no starting material was detected by LC-MS. The reaction mixture was filtered and the filtrate was concentrated. The residue was purified by silica gel (40 g) column chromatography eluting with a gradient of EtOAc (0-60%) in hexane to give the title compound as a foam (420 mg, 75%). LC/MS (method A): retention time=3.24 min, $(M+H)^+=506$.

1G. Preparation of Methyl 3-(2-amino-5-phenylpyridin-3-yl)-2-(benzyloxycarbonyl amino) propanoate

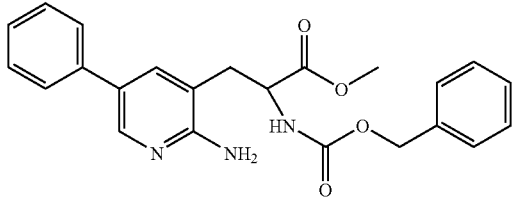

A solution of 1F (456 mg, 0.90 mmol) in TFA (2 mL) and $CH_2Cl_2$ (2 mL) was stirred at RT for 1 h. After this time, no starting material was detected by LC-MS. The reaction was concentrated under reduced pressure. The resulting residue was diluted with $CH_2Cl_2$ (30 mL) and washed with saturated aqueous $NaHCO_3$. The aqueous layer was extracted with $CH_2Cl_2$ (20 mL×2). The combined organic layers were washed with saturated NaCl, dried over $Na_2SO_4$, filtered and concentrated to give the title compound as a white foam (360 mg, 99%). LC/MS (method A): retention time=2.69 min, $(M+H)^+=406$.

1H. Preparation of Benzyl 2-oxo-6-phenyl-1,2,3,4-tetrahydro-1,8-naphthyridin-3-ylcarbamate

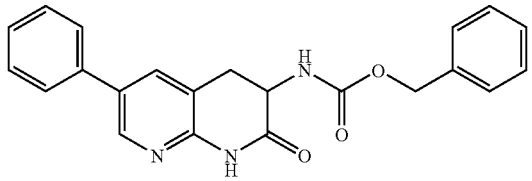

A solution of 1G (356 mg, 0.878 mmol) and p-toluenesulfonic acid monohydrate (16.7 mg, 0.088 mmol) in toluene (8 mL) was heated at 110° C. in a preheated oil bath, a white solid formed after heating for 10 min. The reaction was stirred for additional 20 min, and then cooled to RT. The product was collected by filtration and the solid washed with toluene (5 mL) to give the title compound as a white solid (240 mg, 73%). LC/MS (method A): retention time=3.37 min, (M+H)⁺=374.

1I. Preparation of Benzyl 1-benzyl-2-oxo-6-phenyl-1,2,3,4-tetrahydro-1,8-naphthyridin-3-ylcarbamate

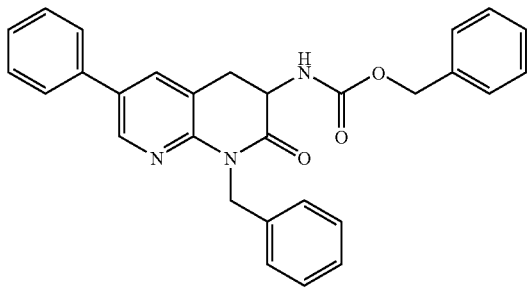

To a solution of 1H (240 mg, 0.64 mmol) in DMF (6 mL) was added cesium carbonate (523 mg, 1.6 mmol), followed by benzyl bromide (0.23 mL, 1.92 mmol). The reaction mixture was stirred at 50° C. for 30 min. After cooling to RT, water was added and the mixture was extracted with EtOAc (2×30 mL). The combined organics were washed with saturated NaCl, dried over Na₂SO₄, filtered and concentrated. The residue was purified by silica gel (40 g) column chromatography eluting with a gradient of EtOAc (0-60%) in hexane to give the title compound as a white solid (270 mg, 91%). LC/MS (method A): retention time=4.09 min, (M+H)⁺=464.

1J. Preparation of 3-Amino-1-benzyl-6-phenyl-3,4-dihydro-1,8-naphthyridin-2(1H)-one

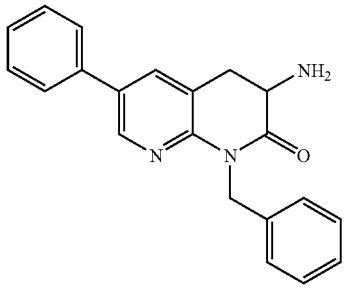

To a solution of 1I (170 mg, 0.367 mmol) in THF (5 mL) and MeOH (5 mL) at RT was added palladium 5% wt. on activated carbon (85 mg). The reaction mixture was stirred under a hydrogen balloon for 1h. The reaction was filtered and the filtrate concentrated to give the title compound as a light yellowish oil (120 mg, 100%). LC/MS (method A): retention time=3.07 min, (M+H)⁺=330.

1K. Preparation of N-(1-Benzyl-2-oxo-6-phenyl-1,2,3,4-tetrahydro-1,8-naphthyridin-3-yl)benzenesulfonamide

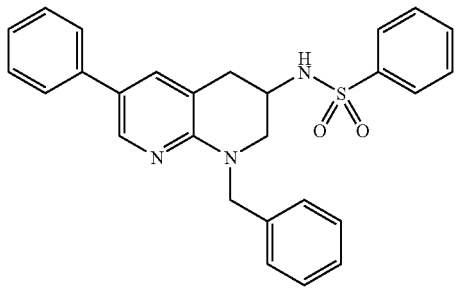

To a solution of 1J (120 mg, 0.36 mmol) in CH₃CN (4 mL) at RT was added DIPEA (94 μL, 0.54 mmol), followed by benzenesulfonyl chloride (51 μL, 0.4 mmol). After 5 min, white precipitates formed. The reaction was stirred for additional 15 min. The product was collected by filtration and the solid washed with CH₃CN (2-3 mL) to give the title compound as a white solid (100 mg, 71%). LC/MS (method A): retention time=3.96 min, (M+H)⁺=470. ¹H NMR (CD₃SOCD₃, 400 MHz): δ8.60 (d, J=2.3 Hz, 1H), 8.35 (s, 1H), 7.07 (d, J=2.2 Hz, 1H), 7.94 (dd, J₁=7.1 Hz, J₂=1.5 Hz, 2H), 7.70 (dd, J₁=8.5 Hz, J₂=1.3 Hz, 2H), 7.66-7.69 (m, 1H), 7.61-7.64 (m, 2H), 7.54 (t, J =7.5 Hz, 2H), 7.34-7.46 (m, 1H), 7.25 -7.34 (m, 5H), 5.16 (dd, J₁=47.0 Hz, J₂=15.2 Hz, 2H), 4.44-4.50 (m, 1H), 3.20 (dd, J₁=15.9 Hz, J₂=6.0 Hz), 3.06-3.13 (m, 1H).

Example 2

Preparation of N-(1-Benzyl-6-phenyl-1,2,3,4-tetrahydro-1,8-naphthyridin-3-yl)benzenesulfonamide

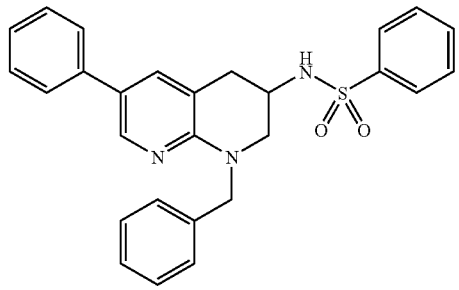

To a suspension of 1K (80 mg, 0.17 mmol) in THF (1 mL) at RT under argon was added borane-tetrahydrofuran complex (0.85 mL, 0.85 mmol) dropwise. After the addition, the reaction became a clear solution. The reaction was allowed to stir at RT under argon for 30 min. After this time, no starting material was detected by LC-MS. MeOH (1 mL) was added carefully to the reaction and the reaction mixture was stirred at RT for 40 min, then concentrated under reduced pressure. The residue was partitioned between CH₂Cl₂ and saturated aqueous NaHCO₃. The layers were separated. The aqueous layer was extracted with CH₂Cl₂ (20 mL). The combined organics were washed with saturated NaCl, dried over Na₂SO₄, filtered and concentrated. The resultant residue was purified by silica gel (10 g) column chromatography eluting with a gradient of EtOAc (0-50%) in hexane to give the title compound as a white foam (74 mg, 96%). LC/MS (method A): retention time=3.96 min, (M+H)⁺=456. ¹H-NMR (CDCl₃, 400 MHz): δ8.30 (s, 1H), 7.70 (dd, J₁=8.2 Hz, J₂=1.2 Hz, 2H), 7.52-7.60 (m, 1H), 7.40-7.52 (m, 6H), 7.20-7.40 (m, 7H), 4.75 (dd, J₁=48.2. Hz, J₂=15.0 Hz, 2H), 4.71 (d, J=8.6 Hz, 1H), 3.80-3.92 (m, 1H), 3.30 (dd, J₁=15.9 Hz, J₂=2.2 Hz, 1H), 3.00-3.13 (m, 2H), 2.75-2.85 (m, 1H).

Example 3

Preparation of N-(1-Benzyl-2-oxo-6-phenyl-1,2,3,4-tetrahydro-1,7-naphthyridin-3-yl)benzenesulfonamide

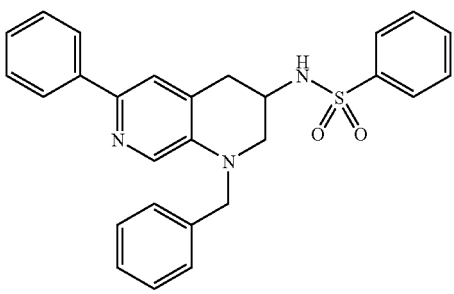

3A. Preparation of tert-Butyl 6-bromopyridin-3-ylcarbamate

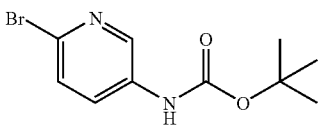

To a solution of 3-amino-6-bromopyridine (8.65 g, 50 mmol) in THF (100 mL) at 0° C. was added sodium bis(trimethylsilyl)amide (1 M solution in THF, 105 mL, 105 mmol). After addition, the reaction was stirred at 0° C. for 5 min, and then di-tert-butyl dicarbonate (12 g, 55 mmol) was added in several portions. After addition, the reaction was stirred at RT for 30 min, and then diluted with water (60 mL) and neutralized by adding ice-cold 1N HCl (about 90 mL) to pH=7~8. The resultant mixture was extracted with EtOAc (3×100 mL). The combined organics were washed with saturated NaCl, dried (Na$_2$SO$_4$), filtered and concentrated. The resulting residue was purified by silica gel (330 g) column chromatography eluting with a gradient of EtOAc (0-50%) in hexane to give the title compound as an off-white solid (11.6 g, 85%). LC/MS (method A): retention time=3.47 min, (M+H–tBu))$^+$=217.

3B. Preparation of tert-Butyl 6-phenylpyridin-3-ylcarbamate

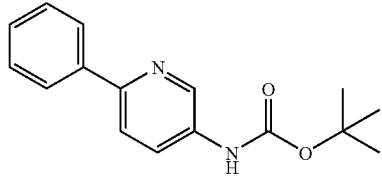

To a solution of 3A (8.3 g, 30.3 mmol) in THF (50 mL)-MeOH (50 mL) at RT was added phenylboronic acid (7.44 g, 61 mmol), PXPd (489 mg, 0.91 mmol), followed by K$_2$CO$_3$ (16.75 g, 121 mmol). The reaction mixture was stirred at 70° C. in a preheated oil bath for 1h. After this time, the reaction mixture was cooled to RT. The reaction mixture was poured into water (100 mL), and the resultant mixture was extracted with EtOAc (3×100 mL). The combined organics were washed with saturated NaCl, dried (Na$_2$SO$_4$), filtered and concentrated. The resulting residue was triturated with 30% EtOAc in hexane. The solid was collected by filtration to give the title compound as an off-white solid (5.6 g, 68%). LC/MS (method A): retention time=2.83 min, (M+H)$^+$=271.

3C. Preparation of tert-Butyl 4-formyl-6-phenylpyridin-3-ylcarbamate

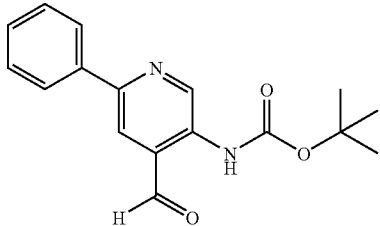

A solution of 3B (3.3 g, 12.21 mmol) in dry THF (50 mL) and TMEDA (4.6 mL, 30.53 mmol) under argon was cooled to –72° C. and treated dropwise with n-butyllithium (2.5 M in hexanes, 12.2 mL, 30.53 mmol) at such a rate so that the temperature did not exceed –65° C. Upon completion of the addition, the reaction was stirred at –72° C. for an additional 15 min and then at –20° C. for 1.5 h. The reaction was cooled again to –72° C., and N-formyl piperidine (2.7 mL, 24.4 mmol) was added while the temperature was maintained below –65° C. The mixture was allowed to stir at RT for 30 min. After this time, no starting material was detected by LC-MS. The solution was cooled to 0° C. and quenched by the addition of 1 M aqueous HCl to bring the pH to 6-8. The reaction was stirred at RT for 15 min, extracted with EtOAc (3×100 mL). The combined organics were washed with saturated NaCl, dried over Na$_2$SO$_4$, filtered, and evaporated under reduced pressure. The residue was purified by silica gel (110 g) column chromatography, eluting with a gradient of EtOAc (0-60%) in hexane to give the title compound as a yellow solid (1.6 g, 44%). LC/MS (method A): retention time=2.79 min, (M+MeOH+H)$^+$=331.

3D. Preparation of (Z)-Methyl 2-(benzyloxycarbonylamino)-3-(5-(tert-butoxycarbonyl amino)-2-phenylpyridin-4-yl)acrylate

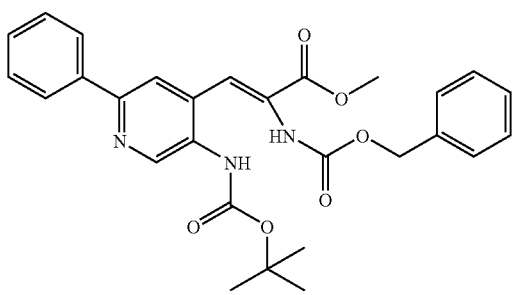

To a slurry of 60% of sodium hydride (228 mg, 5.7 mmol) in THF (17 mL) at 0° C. was added 1A (1.88 g, 5.24 mmol) in several portions over 10 min. The reaction mixture was then brought to RT for 20 min, then cooled again at 0° C. A suspension of 3C (1.42 g, 4.76 mmol) in THF (17 mL) was added over 10 min at 0C, then the reaction was warmed up to RT. After stirring for 20 min, the reaction was quenched with water (40 mL). The aqueous layer was extracted with EtOAc (50 mL×2). The combined EtOAc extracts were dried (Na$_2$SO$_4$), filtered and concentrated. The resulting residue was purified by silica gel (110 g) column chromatography eluting with a gradient of EtOAc (0-60%) in hexane to give the title compound as an off-white solid (1 g, 42%). LC/MS (method A): retention time=3.33 min, (M+H)$^+$=504.

3E. Preparation of Methyl 2-(benzyloxycarbonylamino)-3-(5-(tert-butoxycarbonyl amino)-2-phenylpyridin-4-yl)propanoate

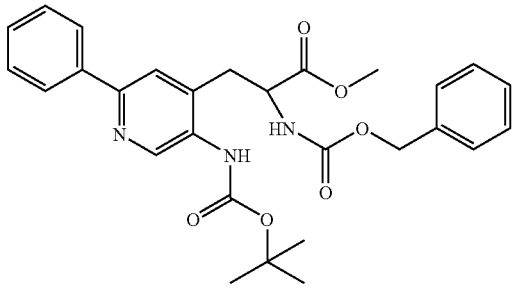

A suspension of 3D (1.1 g, 2.18 mmol) and platinium 5% wt. on activated carbon (800 mg) in THF (80 mL) and MeOH (80 mL) was stirred at RT under $H_2$ at 70 psi for 2 days. After this time, no starting material was detected by LC-MS. The reaction mixture was filtered and the filtrate was concentrated to give the title compound as an off-white foam (1.04 g, 94%). LC/MS (method A): retention time=3.19 min $(M+H)^+=506$.

3F. Preparation of Benzyl 2-oxo-6-phenyl-1,2,3,4-tetrahydro-1,7-naphthyridin-3-ylcarbamate

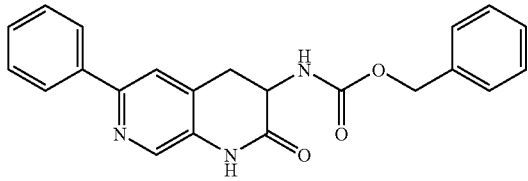

A solution of 3E (980 mg, 1.94 mmol) in TFA (2 mL) and $CH_2Cl_2$ (2 mL) was stirred at RT for 2 h. After this time, no starting material was detected by LC-MS. The reaction was concentrated under reduced pressure. The resulting residue was diluted with EtOAc (30 mL) and washed with saturated aqueous $NaHCO_3$. The aqueous layer was extracted with EtOAc (30 mL×3). The combined organic layers were washed with saturated NaCl, dried over $Na_2SO_4$, filtered and concentrated. The resulting residue was purified by silica gel (40 g) column chromatography eluting with a gradient of EtOAc (30-100%) in hexane to give the title compound as a white solid (470 mg, 65%). LC/MS (method A): retention time=2.72 min, $(M+H)^+=374$.

3G. Preparation of Benzyl 1-benzyl-2-oxo-6-phenyl-1,2,3,4-tetrahydro-1,7-naphthyridin-3-ylcarbamate

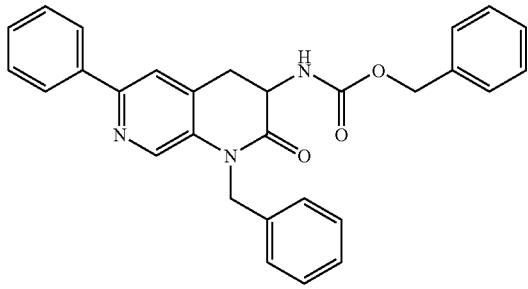

To a solution of 3F (400 mg, 1.07 mmol) in DMF (8 mL) was added cesium carbonate (873 mg, 2.68 mmol), followed by benzyl bromide (0.38 mL, 3.21 mmol). The reaction mixture was stirred at 50° C. for 1 h. After cooling to RT, water (100 mL) was added. The reaction mixture was extracted with EtOAc (3×30 mL). During the extraction, some precipitates formed. The solid was collected by filtration and washed with EtOAc to give the title compound (250 mg). The combined organics were washed with saturated NaCl, dried over $Na_2SO_4$, filtered and concentrated. The resultant residue was purified by silica gel (40 g) column chromatography eluting with a gradient of EtOAc (0-60%) in hexane to give additional 160 mg of the title compound (total 410 mg, 83%) as a white solid. LC/MS (method A): retention time=3.55 min, $(M+H)^+=464$.

3H. Preparation of 3-Amino-1-benzyl-6-phenyl-3,4-dihydro-1,7-naphthyridin-2(1H)-one

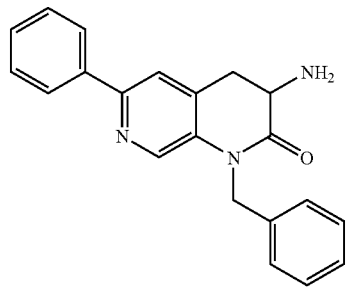

To a solution of 3G (300 mg, 0.65 mmol) in THF (80 mL) and MeOH (80 niL) at RT was added palladium 5% wt. on activated carbon (150 mg). The reaction mixture was stirred under a hydrogen balloon for lh. The reaction was filtered and the filtrate concentrated to give the title compound as a foam (144 mg, 91%). LC/MS (method A): retention time=2.37 min, $(M+H)^+=330$.

3I. Preparation of N-(1-Benzyl-2-oxo-6-phenyl-1,2,3,4-tetrahydro-1,7-naphthyridin-3-yl)benzenesulfonamide

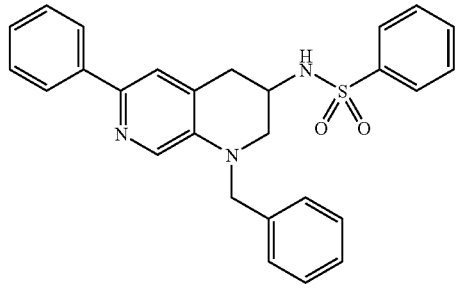

To a solution of 3H (120 mg, 0.36 mmol) in $CH_3CN$ (8 mL) at RT was added DIPEA (94 µL, 0.54 mmol), followed by benzenesulfonyl chloride (51 µL, 0.4 mmol). After 5 min, white precipitates formed. The reaction was stirred for additional 20 min. The product was collected by filtration and the solid washed with $CH_3CN$ (5 mL) to give the title compound as a white solid (100 mg, 71%). LC/MS (method A): retention time=3.30 min, $(M+H)^+=470$. $^1$H NMR $(CD_3SOCD_3$, 400 MHz): δ8.30 (s, 1H), 8.23 (s, 1H), 7.94 (dd, $J_1=8.6$ Hz, $J_2=1.4$ Hz, 2H), 7.75-7.85 (m, 3H), 7.50-7.65 (m, 3H), 7.40 (t, J=7.4 Hz, 2H), 7.15-7.38 (m, 6H), 7.54 (t, J=7.5 Hz, 2H), 7.34-7.46 (m, 1H), 7.25 -7.34 (m, 5H), 5.13 (s, 2H), 4.30-4.42 (m, 1H), 3.00-3.20 (m, 2H).

Example 4

Preparation of N-(1-Benzyl-6-phenyl-1,2,3,4-tetrahydro-1,7-naphthyridin-3-yl)benzenesulfonamide

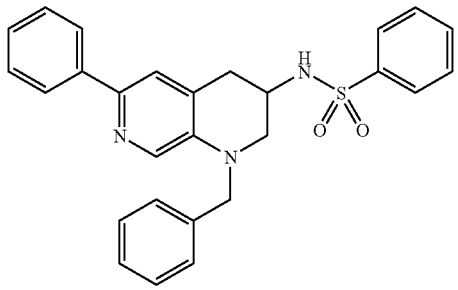

To a suspension of 3I (80 mg, 0.17 mmol) in THF (1 mL) at RT under argon was added borane-tetrahydrofuran complex (0.85 mL, 0.85 mmol) dropwise. After the addition, the reaction became a clear solution. The reaction was allowed to stir at RT under argon for 1 h. After this time, no starting material was detected by LC-MS. MeOH (1 mL) was added carefully to the reaction and the reaction was stirred at RT for overnight. The solvent was concentrated. The resultant residue was partitioned between $CH_2Cl_2$ and saturated aqueous $NaHCO_3$ (20 mL). The layers were separated. The aqueous layer was extracted with $CH_2Cl_2$ (20 mL×3). The combined organics were washed with saturated NaCl, dried over $Na_2SO_4$, filtered and concentrated. The resultant residue was purified by silica gel (10 g) column chromatography eluting with a gradient of EtOAc (0-60%) in hexane to give the title compound as a white foam (71 mg, 88%). LC/MS (method A): retention time=2.69 min, $(M+H)^+$=456. $^1$H-NMR ($CDCl_3$, 400 MHz): δ8.00 (s, 1H), 7.75-7.85 (m, 4H), 7.47-7.55 (m, 1H), 7.10-7.48 (m, 11H), 5.44 (d, J=8.2 Hz, 1H), 4.30 (dd, $J_1$=90 Hz, $J_2$=16.4 Hz, 2H), 3.80-3.90 (m, 1H), 3.35-3.45 (m, 1H), 3.10 (dd, $J_1$=4.9 Hz, $J_2$=1.8 Hz, 1H), 2.93 (dd, $J_1$=16.7 Hz, $J_2$=4.5Hz, 1H), 2.65 (dd, $J_1$=4.9 Hz, $J_2$=1.8 Hz, 1H).

Example 5

Preparation of N-(8-Benzyl-3-phenyl-5,6,7,8-tetrahydropyrido[2,3-c]pyridazin-6-yl)benzenesulfonamide

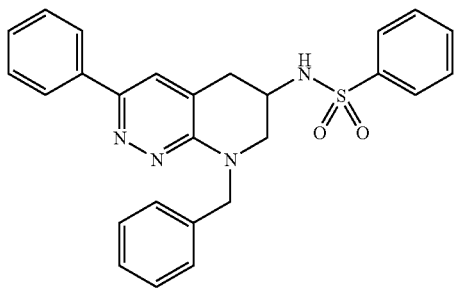

5A. Preparation of 2-Methylene-4-oxo-4-phenylbutanoic acid

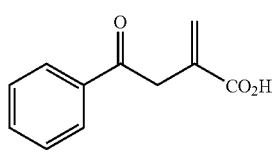

To a stirred slurry of benzene (4.50 mL, 50.3 mmol) and itaconic anhydride (5.64 g, 50.3 mmol) in 1,2-dichloroethane at room temperature under argon, was added aluminum chloride (13.42 g, 100.7 mmol) in portions over 30 min A dark green solution formed as the temperature rose to 27° C. before subsiding. After 4 h, the now brown solution was poured rapidly into a stirred mixture of ice (200 g) and concentrated hydrochloric acid (15 mL). The resulting beige solids were filtered and air-dried to give the title compound (4.69 gm, 49%). MS $[M+H]^+$: found 191.

5B. Preparation of 4-Methyl-6-phenylpyridazin-3-ol

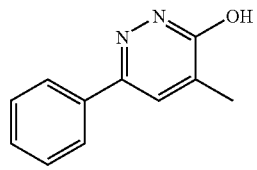

To a stirred solution of compound 5A, (4.48 g, 23.6 mmol) in 50 mL of methanol at 35° C. under argon was added hydrazine (0.75 mL, 35.3 mmol) over 5 min The reaction mixture was then heated to reflux under argon for 2 h, as a precipitate formed. The reaction mixture was then cooled and evaporated under reduced pressure. The solid residue was slurried in isopropanol, filtered and air-dried to give 4-methyl-6-phenylpyridazin-3-ol (2.66 gm, 61%) as a yellow solid. MS $[M+H]^+$: found 187.

5C. Preparation of 3-Bromo-4-methyl-6-phenylpyridazine and 3-bromo-4-(bromomethyl)-6-phenylpyridazine

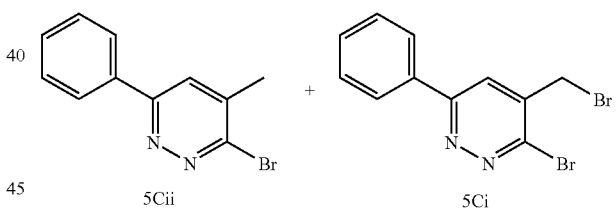

5Cii       5Ci

A stirred mixture of compound 5B (2.66 g, 14.3 mmol) and phosphoryl bromide (6.44 g, 22.5 mmol) in a round-bottom flask fitted with a calcium-chloride filled drying tube was placed into an oil bath pre-heated to 130° C. After 4 h, the gummy red-black reaction mixture was removed from the oil bath and cooled to room temperature. Ice chips (~40 g) were added and the resulting slurry was slowly treated with 50% potassium hydroxide until the solution reached pH 8. The mixture was extracted twice with dichloromethane. The organic extracts were combined, washed. with water, dried ($MgSO_4$), filtered and evaporated in vacuo. Purified by flash chromatography (1:49 ether/dichloromethane, followed by 7:93 ether/dichloromethane) to give two fractions: the least polar material, 3-bromo-4-(bromomethyl)-6-phenylpyridazine (0.195 g, 4%) as a colorless oil (5Ci) and then 3-bromo-4-methyl-6-phenylpyridazine (1.48 g, 42%) as a yellow oil (5Cii). MS: (5Ci) $[M+H]^+$, found 327; MS: (5Cii) $[M+H]^+$, found 249.

5D. Preparation of tert-Butyl 2-((3-bromo-6-phenylpyridazin-4-yl)methyl)-3-oxobutanoate

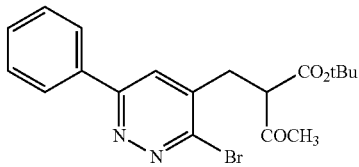

To a stirred solution of compound 5Ci (0.188 g, 0.58 mmol) in 3 mL of dichloromethane at room temperature was added tert-butyl acetoacetate (0.184 mg, 1.16 mmol) and then tetrabutylammonium bromide (0.037 g, 0.12 mmol). The solution was cooled to −78° C. and 2-tert-butylimino-2-diethylamino-1,3-dimethylperhydro-1,3,2-diazaphosphorine (0.25 mL, 0.87 mmol) was added over 30 sec. After 1 h, the reaction mixture was warmed to 0° C. in situ. The reaction mixture was then quenched with 10% citric acid solution and extracted twice with dichloromethane. The combined organic extracts were dried ($Na_2SO_4$), filtered and evaporated under reduced pressure. Purification by silica gel chromatography (1:19 Ether/$CH_2Cl_2$) provided the title compound, tert-butyl 2-((3-bromo-6-phenylpyridazin-4-yl)methyl)-3-oxobutanoate (0.162 g, 69%) as a yellow oil. MS [M+H]$^+$: found 405.

5E. Preparation of tert-Butyl 2-((3-bromo-6-phenylpyridazin-4-yl)methyl)acrylate

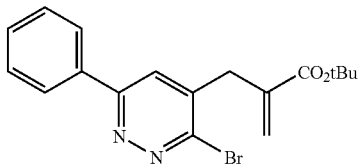

To a stirred solution of compound 5D, (0.160 g, 0.39 mmol) in 3 mL of THF at room temperature under argon was added 0.43 mL (in THF, 0.43 mmol) of 1M lithium bis(trimethylsilyl)amide over 2 min and, after 20 min, powdered, dry paraformaldehyde (0.059 mg, 1.97 mmol). The cooling bath was removed and the reaction mixture was stirred at room temperature for 3 h. The reaction mixture was then quenched with saturated NaCl and extracted twice with dichloromethane. The combined organic extracts were dried over $MgSO_4$, filtered and evaporated under reduced pressure. Purification by silica gel chromatography (7:93 Ether/$CH_2Cl_2$) provided the title compound, tert-butyl 2-((3-bromo-6-phenylpyridazin-4-yl)methyl)acrylate (0.142 g, 97%) as a light yellow oil. MS [M+H]$^+$: found 375.

5F. Preparation of tert-Butyl 8-benzyl-3-phenyl-5,6,7,8-tetrahydropyrido[2,3-c]pyridazine-6-carboxylate

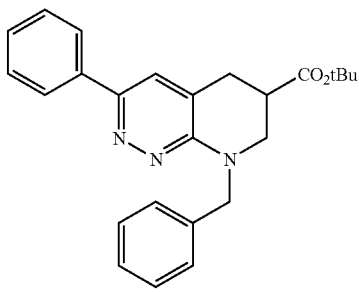

To a stirred solution of compound 5E, (0.140 g, 0.37 mmol) in 1.5 mL of isopropanol at room temperature under argon was added (in one portion) benzylamine (0.055 mL, 0.50 mmol). After 15 h, the reaction mixture was heated to 65° C. for 4 h and then to 85° C. for 15 h. The reaction mixture was then cooled to room temperature and the solvent removed at reduced pressure. The residue was dissolved in EtOAc and washed once with saturated sodium bicarbonate solution. The organic extract was dried over $Na_2SO_4$, filtered and evaporated under reduced pressure. Purification by silica gel chromatography (1:9 Ether/$CH_2Cl_2$) provided the title compound, tert-butyl 8-benzyl-3-phenyl-5,6,7,8-tetrahydropyrido[2,3-c]pyridazine-6-carboxylate, as a light yellow solid (0.084 g, 57%). MS [M+H]+: found 402.

5G. Preparation of Benzyl 8-benzyl-3-phenyl-5,6,7,8-tetrahydropyrido[2,3-c]pyridazin-6-ylcarbamate

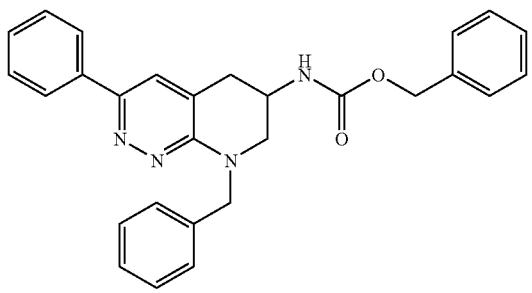

A solution of compound 5F (0.083 g, 0.207 mmol) in 1.5 mL of 1:2 TFA/dichloromethane) was stirred at room temperature for 3 h, evaporated under reduced pressure and re-evaporated from carbon tetrachloride. The yellow oil was dissolved in ethyl acetate, washed with 10% citric acid and the aqueous layer re-extracted with EtOAc. The organic extracts were combined, dried ($MgSO_4$) and evaporated to give a yellow semi-solid. The solid was treated with saturated sodium bicarbonate solution and then brought to pH 6 with 1 M hydrochloric acid. The aqueous phase was extracted twice with EtOAc. The extracts were combined, dried ($MgSO_4$), filtered and evaporated to give a yellow solid. This solid was slurried in 1.0 mL of dioxane and DPPA (0.031 mL, 0.144 mmol), triethylamine (0.021 mL, 0.151 mmol) and benzyl alcohol (0.015 mL, 0.145 mmol) were added. After 20 min at room temperature, the mixture was heated to reflux for 15 h. The resulting deep red solution was cooled, diluted with EtOAc, washed once with saturated sodium bicarbonate solution, dried ($MgSO_4$), filtered and evaporated. Purification by silica gel chromatography (7:93 Ether/$CH_2Cl_2$) provided the title compound benzyl 8-benzyl-3-phenyl-5,6,7,8-tetrahydropyrido[2,3-c]pyridazin-6-ylcarbamate as a red solid (0.024 g, 44%). MS [M+H]$^+$: found 451.

5H. Preparation of N-(8-Benzyl-3-phenyl-5,6,7,8-tetrahydropyrido[2,3-c]pyridazin-6-yl)benzenesulfonamide

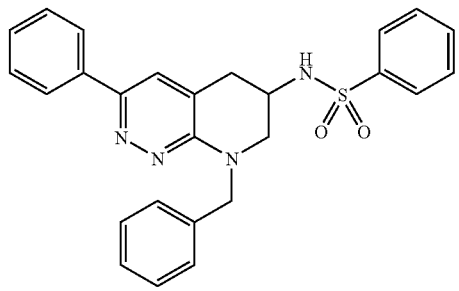

To a stirred solution of 5G (0.023 g, 0.051 mmol) in 0.3 ML of acetonitrile at room temperature under argon was added iodotrimethylsilane (0.020 mL, 0.144 mmol). The yellow solution was stirred 20 min and then quenched with methanol (2 mL). After stirring for 30 min, the reaction mixture was evaporated and then re-evaporated from dichloromethane/hexanes. The solid residue was slurried twice with ether, decanting each time. The remaining solid was slurried in 10% sodium carbonate solution (1.0 mL) at room temperature while a solution of benzenesulfonyl chloride (0.020 mL, 0.157 mmol) in 1.0 mL of THF was added. After rapid stirring for 15 h, the reaction mixture was diluted with water. The solution was adjusted to pH 8 with a few drops of hydrochloric acid and then extracted twice with EtOAc. The organic extracts were dried ($MgSO_4$), filtered, evaporated and purified by chromatography on silica gel (1:5 Ether/$CH_2Cl_2$) to give the title compound as a yellow solid (16.5 mg, 71% yield). MS [M+H]$^+$: found 457. HPLC (Method C): retention time, 7.33 min; 98.3% purity. $^1$H NMR ($CDCl_3$, 400 MHz) δ7.90 (m, 2H), 7.77 (m, 2H), 7.54 (m, 1H), 7.49-7.37 (m, 5H), 7.32-7.21 (m, 6H), 5.61 (d, 1H, J=8.0 Hz), 5.09 (d, 2H, J=14.9 Hz), 4.59 (d, 2H, J=14.9 Hz), 3.84 (m, 1H), 3.33 (dd, 1H, J=2.6, 11.3 Hz), 3.09 (m, 1H), 2.90 (dd, 2H, J=4.4, 17.1 Hz), 2.77 (dd, 2H, J=3.1, 17.1 Hz); $^{13}$C NMR ($CDCl_3$, 101 MHz) δ155.5, 151.2, 140.7, 137.3, 136.3, 132.7, 129.2, 128.8, 128.7, 128.3, 127.6, 126.9, 125.9, 125.9, 124.9, 51.3, 51.0, 44.8, 33.6.

BIOLOGICAL EVALUATION

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 µl. 5 µg of membranes were brought up to a final volume of 95 µl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25× PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding $K_i$ values of the working Examples fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to preincubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

UTILITIES AND COMBINATIONS

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-inducd hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, C1-101 1 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Lett*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8 gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: application Ser. No. 09/097,338, filed Jun. 15, 1998; application Ser. No. 09/094,797, filed Jun. 15, 1998; application Ser. No. 09/173,413, filed Oct. 15, 1998; and application Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine*, 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound or a pharmaceutically acceptable salt or a stereoisomer according to Formula I:

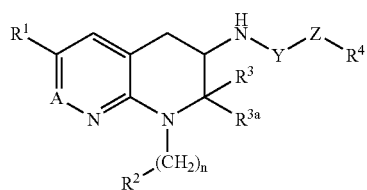

wherein,
one of A or B is N and the other is CH;
Y is selected from the group consisting of CO and $S(O)_2$;
Z is selected from the group consisting of a direct bond, oxygen, $NR^8$ and alkyl;
$R^1$ is selected from the group consisting of hydrogen, alkyl, alkenyl, alkynyl, cycloalkyl, cycloalkylalkyl, heterocyclyl, heterocycloalkyl, aryl, heteroaryl, arylalkyl, heteroarylalkyl, halo, $CF_3$, CN, $OR^5$, $NR^6R^{6a}$;
$R^2$ is selected from the group consisting of alkyl, alkenyl, alkynyl, cycloalkyl, heterocyclyl, aryl, heteroaryl, $COOR^7$ and $CONR^7R^{7a}$;
$R^3$ and $R^{3a}$ are hydrogen or $R^3$ and $R^{3a}$ taken together form a double bond with oxygen;
$R^4$ is selected from the group consisting of alkyl, alkenyl, alkynyl, cycloalkyl, cycloalkylalkyl, heterocyclyl, heterocycloalkyl, aryl, arylalkyl and heteroarylalkyl;
$R^5$ is selected from the group consisting of alkyl, alkenyl, alkynyl, cycloalkyl, cycloalkylalkyl, heterocyclyl, heterocycloalkyl, aryl, heteroaryl, arylalkyl, heteroarylalkyl, $CHF_2$ and $CF_3$;
$R^6$ and $R^{6a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;
or $R^6$ and $R^{6a}$ taken together can form cycloalkyl or heterocyclyl;

$R^7$ and $R^{7a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;
or $R^7$ and $R^{7a}$ taken together can form cycloalkyl or heterocyclyl;
$R^8$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;
or $R^4$ and $R^8$ taken together can form cycloalkyl or heterocyclyl;
n is an integer of 0 or 1.

2. The compound according to claim 1 wherein, Y is $-S(O)_2-$.

3. The compound according to claim 2 wherein, Z is a direct bond.

4. The compound according to claim 3 wherein, A is nitrogen; and B is CH.

5. The compound according to claim 4 wherein, n is 1.

6. The compound according to claim 5 wherein, $R^1$ is selected from the group consisting of aryl and heteroaryl.

7. The compound according to claim 6 wherein, $R^2$ is selected from the group consisting of aryl and heteroaryl.

8. The compound according to claim 7 wherein, $R^4$ is aryl.

9. The compound according to claim 3 wherein, A is CH; and B is nitrogen.

10. The compound according to claim 9 wherein, n is 1.

11. The compound according to claim 10 wherein, $R^1$ is selected from the group consisting of aryl and heteroaryl.

12. The compound according to claim 11 wherein, $R^2$ is selected from the group consisting of aryl and heteroaryl.

13. The compound according to claim 12 wherein, $R^4$ is aryl.

14. The compound according to claim 1 wherein the compound is selected from the group consisting of:

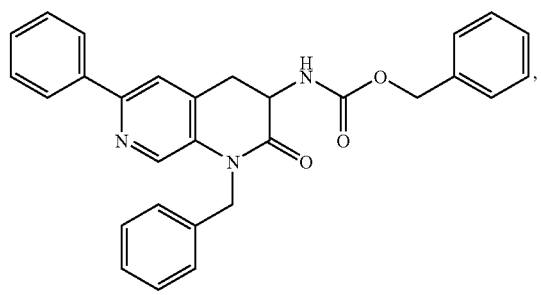

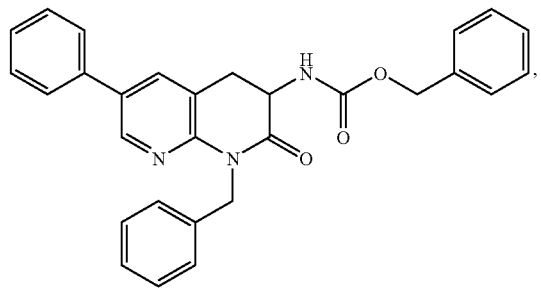

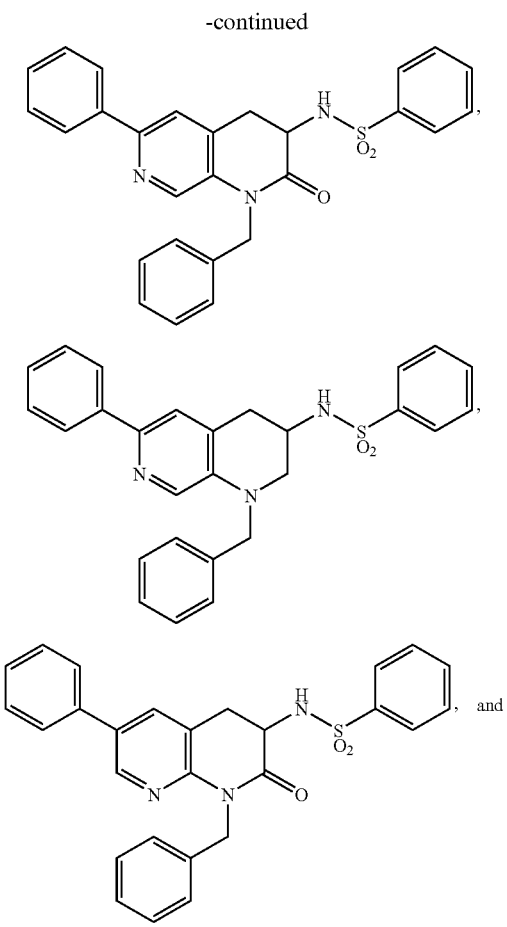

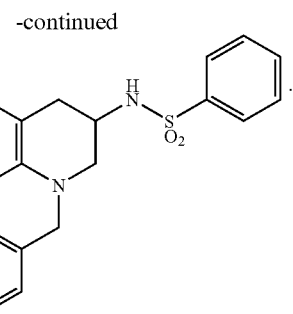

15. A pharmaceutical composition, comprising:
at least one compound according to claim 1; and at least one pharmaceutically acceptable diluent or carrier.

16. The pharmaceutical composition according to claim 15, further comprising at least one additional therapeutic agent selected from the group consisting of anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

17. A method for treating obesity, comprising administering to a patient in need a therapeutically effective amount of a cannabinoid receptor 1 (CB1) antagonist according to claim 1.

18. A method for smoking cessation, comprising administering to a patient in need a therapeutically effective amount of a cannabinoid receptor 1 (CB1) antagonist according to claim 1.

* * * * *

UNITED STATES PATENT AND TRADEMARK OFFICE
CERTIFICATE OF CORRECTION

PATENT NO. : 7,368,458 B2
APPLICATION NO. : 11/330541
DATED : May 6, 2008
INVENTOR(S) : Chongqing Sun, William R. Ewing and Yanting Huang It is certified that error appears in the above-identified patent and that said Letters Patent is hereby corrected as shown below:

Column 13, lines 55 to 65, please delete

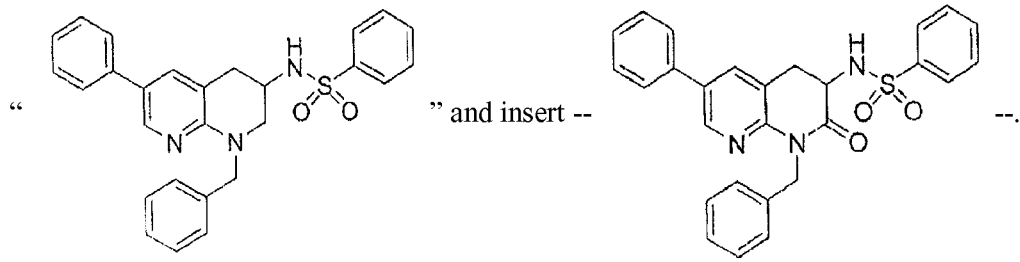

Column 17, lines 55 to 65, please delete

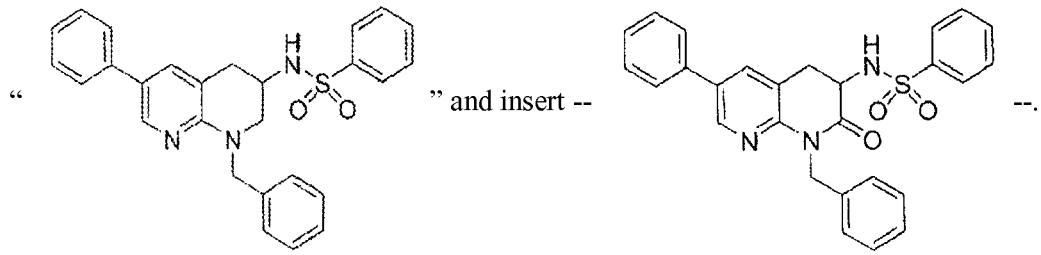

Column 19, lines 6 to 20, please delete

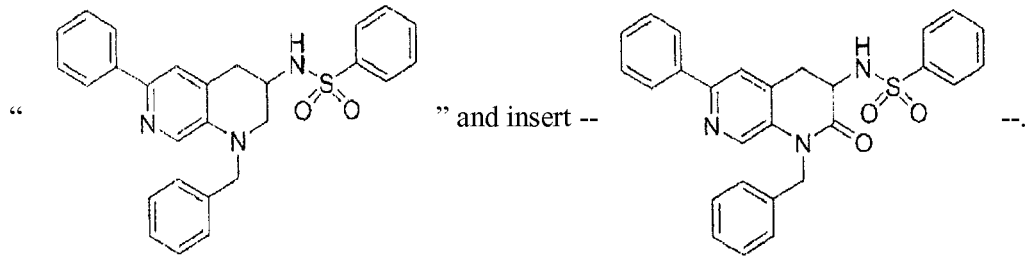

UNITED STATES PATENT AND TRADEMARK OFFICE
CERTIFICATE OF CORRECTION

PATENT NO. : 7,368,458 B2
APPLICATION NO. : 11/330541
DATED : May 6, 2008
INVENTOR(S) : Chongqing Sun, William R. Ewing and Yanting Huang It is certified that error appears in the above-identified patent and that said Letters Patent is hereby corrected as shown below:

Column 22, lines 41 to 54, please delete

" 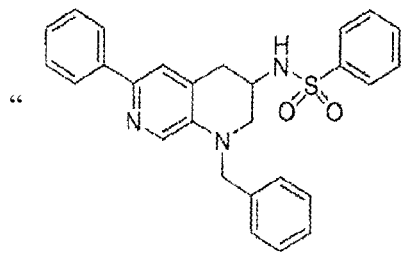 " and insert -- 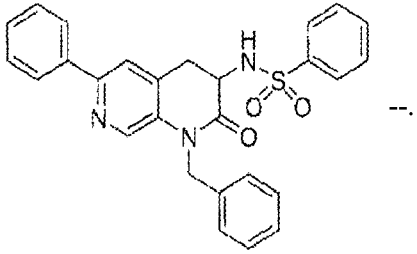 --.

Column 35, line 13, please delete "δ agonist" and insert -- α-agonist --.

Column 36, line 47, please delete "shcizoaffective" and insert -- schizoaffective --.

Signed and Sealed this

Second Day of December, 2008

JON W. DUDAS
*Director of the United States Patent and Trademark Office*